United States Patent [19]

Vold

[11] Patent Number: 4,665,018

[45] Date of Patent: May 12, 1987

[54] METHODS AND TEST KIT FOR DIAGNOSING/MONITORING CANCER IN HUMANS

[75] Inventor: Barbara S. Vold, Menlo Park, Calif.

[73] Assignee: SRI International, Menlo Park, Calif.

[21] Appl. No.: 532,998

[22] Filed: Sep. 16, 1983

Related U.S. Application Data

[63] Continuation-in-part of Ser. No. 371,287, Apr. 23, 1982, abandoned.

[30] Foreign Application Priority Data

Apr. 18, 1983 [WO] PCT Int'l Appl. .................. PCT/US83/00579

[51] Int. Cl.[4] .................. G01N 33/577; G01N 33/574

[52] U.S. Cl. .......................................... 435/6; 435/7; 435/68; 435/172.2; 435/810; 436/536; 436/537; 436/542; 436/548; 436/64; 436/94; 436/804; 436/808; 436/809; 436/813; 436/815; 436/822

[58] Field of Search .................... 424/1.1, 85, 88, 180; 435/4, 6, 7, 68, 172.2, 810; 436/501, 504, 518, 528-534, 536-538, 542, 548, 63, 64, 94, 804, 808-810, 813, 815, 822, 823

[56] References Cited

PUBLICATIONS

Vold, B. S. et al., Cancer Research, vol. 42 (12, part 1), pp. 5265-5269 (1982), Chem. Abst. 98(5):30763s.

Cimino, F. et al., Biochem. SAM Related Compd. Proc. Conf. 1981, pp. 409-412, MacMillan, London UK (1982), in Chem. Abst. 99(1):3656y.

Vold, B. S. Nucleic Acids Research, vol. 7(1), pp. 193-204 (1979), Chem. Abst. 91(25):206763p.

Clark, I. et al., Recent Results Cancer Res., vol. 84, pp. 388-400 (1983) in Chem. Abst. 99(1):3654w.

Thomale, J. et al., Recent Results Cancer Res., vol. 84, pp. 378-387 (1983), in Chem. Abst. 99(1):3653v.

Hirschborn, R. et al., Pediatr. Res., vol. 16(5), pp. 362-369 (1982), in Chem. Abst. 97(1):4522t.

Schoech, G. et al., Clin. Chim. Acta, vol. 108(2), pp. 247-257 (1980), in Chem. Abst. 94(11):79512r.

Gehrke, C. W. et al., J. Chromatography., vol. 188(1), pp. 129-147 (1980), in Chem. Abst. 92(15):124295u.

Uziel, M. et al., NTIS Report & Conf.-760336-1, 34 pages (1976), in Chem. Abst. 85(25):188551n.

Uziel, M. et al., Clin. Chem., vol. 22(9), pp. 1451-1455 (1976), in Chem. Abst. 85(21):1559222f.

Hong, C. I., Biochem. Pharmacol., vol. 22(15), pp. 1927-1936 (1973), "Metabolism of t6A in Rat and Man".

Chheda, G. B., Life Sci., vol. 8 (18 Pt. Z), pp. 979-987 (1969), "Isolation and Characterization of a Novel Nucleoside, t6A, from Human Urine."

Engvall, E., Methods in Enzymology, vol. 70, pp. 419-438 (1980).

Nishimura, S., *Transfer RNA: Structure, Properties, and Recognition,* Shimmel, P. R., et al., eds., Cold Spring Harbor Laboratory (1979), pp. 59-79.

Borek, E., et al., *Cancer Res.* (1977), 37:3362-3366.

Nomura, Y., *FEBS Lett.* (1974), 45:223-227.

Gehrke, C. W., et al., *Cancer Res.* (1979) 39:1150-1153.

Speer, J., et al., *Cancer* (1979) 44:2120-2123.

Borek, E., *Cancer Markers* (1980) ed. Sell, S. Humana Press, pp. 445-462.

Levine, et al., *J. Natl. Cancer Inst.* (1975) 54:341-343.

Milstone, et al., *Nucl. Acids Res.* (1978) 5:3439-3455.

Vold, B., *Nucl. Acids Res.* (1979) 7:193-204, 7:971-980.

*Primary Examiner*—Charles F. Warren
*Assistant Examiner*—Margaret Moskowitz
*Attorney, Agent, or Firm*—Ciotti & Murashige

[57] ABSTRACT

Human cancer is diagnosed/monitored by measuring the levels of certain modified nucleosides, such as N-[(β-D-ribofuranosyl)purin-6-ylcarbamoyl]-L-threonine, in the urine of a subject by a quantitative immunoassay that preferably employs a monoclonal anti-modified nucleoside antibody and comparing that level to the level of the modified nucleoside that occurs in the urine of normal subjects to determine whether the former is substantially elevated over the latter or by comparing that level to the level of the modified nucleoside present in urine specimens taken from the subject at different times.

9 Claims, 3 Drawing Figures

METHODS AND TEST KIT FOR DIAGNOSING/MONITORING CANCER IN HUMANS

REFERENCE TO GOVERNMENT GRANT

The invention described herein was, in part, made in the course of work under a grant from the National Institutes of Health, Department of Health and Human Services, and the National Science Foundation.

CROSS-REFERENCE TO RELATED APPLICATION

This application is a continuation-in-part of copending U.S. application Ser. No. 371,287, filed Apr. 23, 1982, now abandoned.

DESCRIPTION

1. Technical Field

The invention is in the field of cancer diagnosis and monitoring. More particularly it concerns a method for diagnosing cancer or monitoring the status of cancer in patients already diagnosed as having cancer by determining the amount of certain modified nucleosides in urine by immunoassay.

2. Background Art

Ribonucleic acids (RNAs), particularly transfer RNAs (tRNAs), contain a variety of modified nucleosides which are formed after transcription of the macromolecule. Nishimura, S., *Transfer RNA: Structure, Properties, and Recognition,* Shimmel, P.R., et al, eds, Cold Spring Harbor Laboratory (1979), reports that over 50 of these modified nucleosides have been isolated and characterized. When these RNAs are degraded, the majority of modified nucleosides do not appear to be catabolized to any extent in animals or humans and are excreted in significant amounts in urine. Since tRNAs are the most highly modified class of RNAs, it has been assumed that turnover of tRNA is the source of excreted modified nucleosides. Evidence for a higher turnover rate for tRNA in tumor tissue and evidence for intracellular scavenging of tRNAs with structural abnormality have been reported. Borek, E., et al, *Cancer Res* (1977) 37:3362–3366 and Nomura, Y., *FEBS Lett* (1974) 45:223–227.

Prior to applicant's invention only six of the fifty plus known naturally occurring modified nucleosides had been reported to be elevated in cancer patients. The six include four methylated nucleosides (1-methylinosine, $N^2$, $N^2$-dimethylguanosine, 2-methylguanosine, and 1-methyladenosine), pseudouridine, and $N^4$-acetylcytidine. The following articles report measuring elevated amounts of these nucleosides in urine of cancer patients by high performance liquid chromatography (HPLC): Gehrke, C. W., et al, *Cancer Res* (1979) 39:1150–1153, Speer, J., et al, *Cancer* (1979) 44:2120–2123, and Borek, E., *Cancer Markers* (1980) Ed. Sell, S. Humana Press. The nucleosides are concentrated from the urine, such as by affinity chromatography before being measured. The serum levels of the $\epsilon$-aminocaproate derivatives of $N^2$,$N^2$-dimethylguanosine and pseudouridine in cancer patients determined by radioimmunoassay have also been reported. Levine, et al, *J Natl Cancer Inst* (1975) 54:341–343.

Radioimmunoassays for various modified nucleosides, including N-[9-($\beta$-D-ribofuranosyl)purin-6-ylcarbamoyl]-L-threonine ($t^6A$), have been used to evaluate the levels of such nucleosides in bacterial tRNAs. Milstone, et al, *Nucl Acids Res* (1978) 5:3439–3455; Vold, B., *Nucl Acids Res* (1979) 7:193–204; and Vold, B. et al, *Nucl Acids Res* (1979) 7:971–980.

A principal object of the present invention is to provide a reproducible, noninvasive method for detecting the presence or status of human cancer based on the levels of modified nucleosides in physiological fluids. This invention uses unfractionated urine as the test physiological fluid and an immunoassay to determine the amount of modified nucleoside in the urine. Another object of the invention is to provide a method for diagnosing human cancer based on the level of N-[9-($\beta$-D-ribofuranosyl)purin-6-ylcarbamoyl]-L-threonine in urine. Still another object is to provide a novel monoclonal anti-$t^6A$ antibody for use in such diagnosis.

DISCLOSURE OF THE INVENTION

One aspect of the invention is a method for detecting cancer in a human patient comprising:

(a) determining the amount of N-[9-($\beta$-D-ribofuranosyl)purin-6-ylcarbamoyl]-L-threonine in the urine of said patient; and (b) comparing said amount with the standard amount of N-[9-($\beta$-D-ribofuranosyl)purin-6-ylcarbamoyl]-L-threonine present in urine of normal human subjects to determine whether said amount is substantially greater than the standard amount.

When this aspect of the invention is used to monitor the status of cancer in a cancer patient the respective amounts of N-[-($\beta$-D-ribofuranosyl)purin-6-ylcarbamoyl-6-threonine in urine samples taken from the patient at predetermined time intervals will be compared.

As regards this aspect, applicant's invention lies in the discovery that $t^6A$ is elevated in the urine of cancer patients rather than in a particular method for detecting $t^6A$. Accordingly, any mode of detection including HPLC and quantitative immunoassay, may be used to practice this aspect.

Another aspect of this invention is a method for detecting cancer in a human patient comprising:

(a) determining the amount of an underivatized modified nucleoside in a sample of unfractionated urine from the patient by a quantitative immunoassay of the sample; and (b) comparing said amount with the standard amount of the underivatized modified nucleoside present in the urine of normal human subjects.

Again when used to monitor the status of cancer comparisons will be made of the respective amounts of underivatized modified nucleoside found in urine samples taken from the patient at predetermined time intervals.

Other aspects are hybridoma ATCC HB 8351, monoclonal antibody from hybridoma ATCC HB 8351 and functional equivalents thereof, and immunoassay kits for determining $t^6A$ that contain said monoclonal antibody or functional equivalents.

MODES FOR CARRYING OUT THE INVENTION

Figure 1:
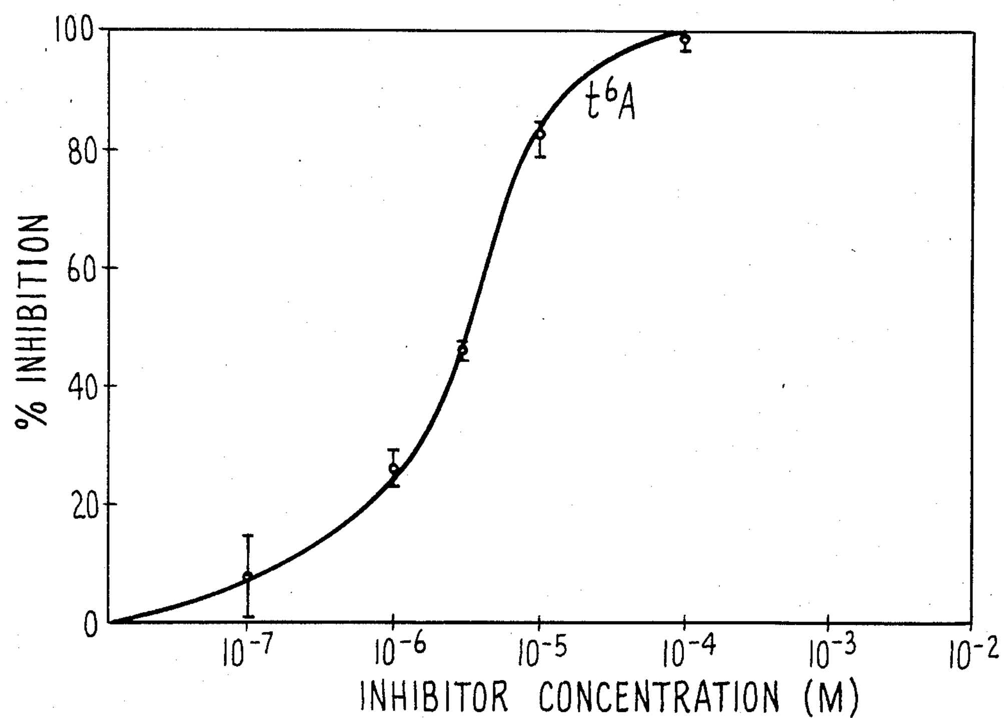
FIG. 1 is a graph showing the results of the radioimmunoassay tests described in Example 2, infra.

The invention methods may be used to diagnose or monitor the status of any type of cellular neoplasm, including carcinomas, myelomas, and lymphomas. These methods are thus useful in diagnosis as in screening programs for early detection of the disease, in therapy as in evaluating the status of the disease after surgical radiation and/or chemotherapeutic treatment and in prognosis such as in detecting the possibility of recurrence or metastases. Examples of cancers that have been determined to be associated with elevated levels of modified nucleosides are leukemia, lung cancer, Burkitt's lymphoma, melanoma, ovarian cancer, metastic breast cancer, Hodgkin's disease, colon cancer, and bladder cancer.

The urine samples that are used in the invention methods may be collected randomly or over a given time period, conventionally 24 hr. It has been reported that no significant variation in the levels of modified nucleoside occurs relative to the sample collection regimen. Fischbein, A. et al, *Cancer Res* (1983) 43:2971–2974. One of the significant advantages of the invention relative to the prior art HPLC method is that the nucleoside does not have to be separated from the urine sample prior to being assayed. In the HPLC technique the nucleosides are separated by affinity chromatography from the sample before being assayed. The nucleosides also do not have to be derivatized as in the prior art serum assays. The amount of urine used in the invention methods will usually range between about 1 to about 100 μl depending upon the particular nucleoside and/or antibody involved.

The modified nucleosides that form the basis for the detection of cancer occur in significantly elevated amounts in the urine of patients having the type of cancer being diagnosed. The modified nucleosides that have been reported to be excreted in elevated amounts by cancer patients are 1-methylinosine, $N^2$,$N^2$-dimethylguanosine, pseudouridine, 1-methyladenosine, $N^4$-acetylcytidine, and 2-methylguanosine. Applicants have found that $t^6A$ is also excreted in elevated amounts by cancer patients. $t^6A$ is a particularly interesting modified nucleoside because it occurs only in tRNA. $t^6A$ is also modified in a different way (addition of threonine) than any of the other modified nucleosides that are known to be elevated in cancer patients.

When the assay is used to monitor the status of cancer in a patient already diagnosed to have cancer, the patient's own levels of modified nucleoside in his/her urine serve as an internal control. Decreases signify a reduction in tumor burden such as might occur after the patient has been treated. Increases signify an increase in tumor burden indicating a recurrence or metastases of the cancer.

The amounts of these modified nucleosides in urine are determined by a quantitative immunoassay. Various types of quantitative immunoassays such as competitive immunoassays, direct immunoassays and indirect immunoassays may be used. The three most common quantitative immunoassays are radioimmunoassay, (both soluble phase and solid phase) quantitative immunofluorescence, and quantitative enzyme assays. Any of these may be used to practice the invention. These assays involve the formation of immune complexes that include a label and the detection of such complexes via the label. As used herein the term "label" is intended to include moieties that may be detected directly such as fluorochromes and radiolabels as well as moieties such as enzymes that must be reacted or derivatized to be detected. In competitive assays the sample is incubated with an antibody against the modified nucleoside and a known amount of labeled modified nucleoside. Any modified nucleoside (unlabeled) in the sample competes with the labeled nucleoside for antibody. The resulting immune complexes are separated and the amount of labeled complex therein is determined. The amount of modified nucleoside is determined by comparison with the effect of standards. Direct immunoassays involve incubating the sample with a labeled antibody against the modified nucleoside and separating any immune complexes that form. The amount of label therein is determined and the amount of modified nucleoside in the sample is determined by comparison with the effect of standards. In an indirect immunoassay, such as an enzyme linked immunosorbent assay (ELISA), the antigen bound to a carrier protein such as an albumin is bound (immobilized) to a solid phase (eg, a tube, bead or well surface), the first antibody is added, and a second enzyme-labeled antibody against the first antibody is added. Immobilized immune complexes are detected via reaction of the enzyme with an appropriate substrate.

The particular label that is used will depend on the type of quantitative immunoassay used. The assay should be such as to provide sensitivities down to at least about 1 to 10 pmol of modified nucleoside. Examples of labels that may be used are radiolabels such as $^{32}P$, $^{125}I$, $^{3}H$, and $^{14}C$, fluorescent labels such as fluorescein and its derivatives, rhodamine and its derivatives, dansyl, and umbelliferone, chemiluminescers such as luciferia and 2,3-dihydrophthalazinediones, and enzymes, such as horseradish peroxidase, alkaline phosphatase, lysozyme, and glucose-6-phosphate dehydrogenase. The antibody or nucleoside, as the case may be, may be tagged with such labels by known methods. For instance, coupling agents such as aldehydes, carbodiimides, dimaleimide, imidates, succinimides, bisdiazotized benzadine, and the like may be used to tag the antibodies with fluorescent, chemi-luminescent, or enzyme labels.

The antibodies against the modified nucleosides that are used in these immunoassays may be polyclonal (heterologous) or monoclonal (homologous). Polyclonal antibodies may be made by immunizing host animals such as mice, rabbits, and sheep using a modified nucleoside-protein carrier conjugate as an immunogen. The immunization will typically involve repeated inoculations with the immunogen, typically at least two at about one week intervals. Such inoculation will raise an immune response against the immunogen and cause the inoculated host's immune system to produce antibodies against the modified nucleoside. Serum from the immunized host will usually be collected about three to ten days after the final booster. Immunoglobulins may be separated from the serum by ammonium sulfate precipitation, gel electrophoresis, dialysis, chromatography, or other conventional separation and purification techniques, if desired.

Monoclonal antibodies against the modified nucleosides may be made by the somatic cell hybridization techniques of Kohler and Milstein, *Nature* (1975) 265:495 using antibody-producing cells, e.g. spleen or lymphoid cells, from the immunized host animal, preferably a mouse, as one of the hybridization partners. The antibody-producing cells are hybridized (fused) with an appropriate cancer (myeloma) cell line using a fusogen such as polyethylene glyocol having a Mw of 1,000 to 6,000 daltons. A myeloma cell line that is sensitive to a selective medium such as HAT medium (Littlefield, *Science* (1969) 145:709–710), fuses efficiently, and will support stable high level expression and secretion of antibody by its hybridization partner is used. While myeloma cells from any species such as those indicated above with respect to polyclonal antibodies may be used, murine and rat myeloma lines having these characteristics are available currently and are preferred. Examples of such lines are those derived from the original MOPC-21 and MPC-11 mouse tumors that are available from the Salk Institute Cell Distribution Center, PO Box 1809, San Diego, Calif. 92112. A myeloma cell:antibody-producing cell ratio in the range of about 1:10 and about 10:1 will normally be used. The individual cell concentrations will typically be in the range of about $10^6$ to $10^8$, preferably $1\times10^7$ to $5\times10^7$, cells/ml fusion medium. Balanced salt solutions containing about 30% to 60% (w/v), preferably 35% to 50% (w/v) fusogen may be used as a fusion medium. After the fusion, the cells are washed with fusogen-free medium to remove fusogen. They are then seeded and cultivated in the selective medium to eliminate unhybridized parent cells and leave only hybrids that are resistant to the selective medium and possess the immortality of the myeloma parent. The cultivation will normally take about three to five weeks.

Surviving hybridomas may be examined for production of antibody against the modified nucleoside by immunoassay. Positive hybridoma clones may be subcloned by limiting dilution techniques and grown in vitro or in vivo by known techniques. The monoclonal anti-modified nucleoside antibody secreted by the subclones may be separated from the culture medium or ascites fluid when grown in vivo by known techniques such as ammonium sulfate precipitation, DEAE cellulose chromatography, or affinity chromatography. Further purification of the antibodies, if desired, may be achieved by ultracentrifugation and microfiltration.

Antibodies against the isotype of the antimodified nucleoside antibody may be used as the labeled second antibody in indirect assays such as the ELISA. For instance if the anti-modified nucleoside antibody is a murine IgG, anti-murine IgG serum from another mammalian species may be used. Such anti-isotype antibodies may be raised by conventional immunization techniques.

The incubations of the immunoassays will be carried out under conditions that permit reaction between the antibody and modified nucleoside. Temperature, pH and duration are the most important process conditions in the incubation. Temperatures in the range of about 5° C. to 40° C., preferably about 37° C., will typically be used. The pH will normally be about 6 to 9, preferably about 7, and the binding reaction will usually reach equilibrium in about 10 min to 2 days, depending upon the particular antibodies and nucleosides involved. Antibody will be used in limiting amounts in the competitive assays. Immune complexes may be separated from the incubation mixture by centrifugation or other conventional techniques. Separation may not be necessary in assays such as the homogeneous enzyme immunoassay (EMIT). Conventional buffer media may be used for any washing steps involved in the assays.

The label detection means used in the immunoassay will depend upon the particular label involved. For instance, radiolabels may be read with scintillation counters, fluorescent labels with fluorescent microscopes (fluorometers) and enzyme labels with colorimeters that detect the magnitude of color change caused by the reaction between the enzyme and the substrate or spectrophotometers (eg, microtiter plate readers).

The basic ingredients of the test kit for carrying out the $t^6A$ radioimmunoassay of the invention are labeled $t^6A$ and monoclonal antibody against $t^6A$. These ingredients will typically be in solution in an appropriate aqueous solvent and contained in suitable dispensers. Solid phase kits will contain a solid phase (tube or bead) and, optionally, a coupling agent such as an aldehyde or carbodimide to bind the antibody to the solid phase. ELISA kits will contain $t^6A$-carrier protein conjugate, anti-$t^6A$ monoclonal antibody, enzyme-labeled antibody against the monoclonal antibody, and a suitable substrate. The kits may also contain a suitable buffer for dilution and washes, carrier protein, unlabled $t^6A$ for preparing standards, a post-coating preparation to reduce nonspecific bonding to solid phase, containers in which the reagents may be used, and directions for performing the assay. The components of the kit may be packaged in a conventional manner.

As indicated above and as illustrated by the examples, infra, in which rabbit anti-$t^6A$ serum and murine monoclonal anti-$t^6A$ antibody are used in the invention, the species of the antibody is not critical. Likewise, as evidenced by the use of rabbit antisera in the invention method (Example 1, infra) the class (subclass) of antibody does not appear to be critical. In this regard although only a single anti-$t^6A$ monoclonal antibody is described in the examples, it is intended that the invention encompass all anti-$t^6A$ monoclonal antibodies, regardless of species or class, that are functionally equivalent to the described monoclonal antibody. Functionally equivalent monoclonal antibodies are those that crossblock (react with the same determinant) the described monoclonal antibody. In this regard the subclasses of IgG differ from one another in their constant region. However, an IgG against a specific antibody will have a functionally equivalent variable region regardless of its subclass. Accordingly, although the exemplified monoclonal antibody is an IgG of a particular subclass, functional monoclonal antibodies of other IgG subclasses or other classes (IgM, IgA, etc) are intended to be within the scope of the invention.

The following examples further illustrate the invention methods. These examples are not intended to limit the invention in any manner.

EXAMPLE 1

Urine Samples 24 hr urine samples were obtained from patients with various advanced malignancies, previously untreated with chemotherapy, and normal volunteers at the Cancer Center of the University of New Mexico. The urines were collected from each individual in plastic containers for 24 h and kept under refrigeration until the end of collection. The urine volume was then measured and an aliquot of urine was kept frozen until the day of analysis. The amount of creatinine for each sample was determined by the colorimetric method described in the Sigma Technical Bulletin No 555 1-12, 1977.

Antibody Preparation

Immunogen was prepared by conjugating $t^6A$ to bovine serum albumin (BSA) using the method of Erlanger and Beiser, PNAS (1964) 52:68–74. Antibodies were made in rabbits, a total of 5 mg immunogen (mixed with complete Freund's adjuvant) per rabbit was introduced in three injections into the hind legs on days 0, 14, and 21. The immunized rabbits were bled on day 28. Serum was precipitated twice at 0° C. with 50% saturated ammonium sulfate (SAS), pH 7.0, and then dialyzed against 0.14 M NaCl, 10 mM sodium phosphate, pH 7.0 (PBS).

Tritiated Antigen.

Tritiated $t^6A$ was prepared by catalytic (Pt) exchange with tritiated water. $[^3H]t^6A$, 0.84 Ci/mmol, was 88% pure by 2D thin layer chromatography analysis using the solvent system described by Rogg, et al, *Nucleic Acids Res* (1976) 3:285-295, and 6.9 pmol was used per assay.

Radioimmunoassay.

The saturated ammonium sulfate radioimmunoassay (SAS-RIA) for $t^6A$ described by Vold, B.S., *Nucleic Acids Res* (1979)7:193-204 was used. Assays were done in 12×75 mm polypropylene tubes in a total reaction volume of 300 μl with 75 mM NaCl, 0.1 M boric acid, 25 mM sodium tetraborate, pH 8.3. Normal rabbit IgG was used to adjust the total protein concentration of each assay to 600 μg. The buffer, antibody, carrier protein, $[^3H]t^6A$, and untreated urine were mixed well, incubated at 37° C. for 1 h, then cooled on ice for 5 min. The amount of urine used was chosen such that normal urine would give inhibition values between 10% and 40%. Thus, 2 μl of urine was used in each assay. An equal volume of ice-cold SAS was added to each tube, mixed thoroughly, and incubated at 0° C. for 30 min. The tubes were then centrifuged at 9,400×g for 15 min at 4° C., and the supernatant removed by aspiration through a capillary pipette. The pellets were resuspended in 200 μl of 50% SAS in borate saline buffer, mixed, centrifuged, and drained as before. The washed pellets were then suspended in 200 μl of 1X borate saline buffer, mixed, and a 75 μl added to 5 ml of Aquasol scintillation fluid. Radioactivity was then measured in a scintillation counter. Under the conditions used for competitive inhibition, cpm bound on the filter without inhibitor and with (or without) antiserum was 1133 (66) for $t^6A$. When urine was added as a source of competitive inhibitor and the same assay repeated on four different occasions, standard deviation was ±3.7%.

The concentration of inhibition present in each urine sample was interpolated from a graph of % trace binding for the antibody when the cognate modified nucleoside had been used as competitive inhibitor. These concentrations were then expressed in mg excreted per 24 hr period and normalized to the creatinine level in each sample expressed as nmol nucleoside/μmol creatinine. Speer, et al, *Cancer* (1979) 44:20-2123.

Urine samples from 8 normal patients, 4 Hodgkins patients, 4 non-Hodgkin's lymphoma patients, 5 lung cancer patients (small cell, adenocarcinoma, squamous cell and large cell) and 8 "other" cancer (breast, head and neck, bowel) patients were tested. None of the patients had been treated previously by chemotherapy. Assay results for the cancer patients were compared by group with the assay results from the normal patients. Significance of variation in the levels of $t^6A$ in the samples was established using a t test comparing each cancer group to the normal group. A P value less than 0.05 was considered a significant variation. The results of these comparisons were:

| Significance of Variation (P) | | | |
|---|---|---|---|
| Lymphomas | | Solid Tumors | |
| Hodgkins | Non-Hodgkins | Lung | Other |
| not significant | $P < 0.05$ | $P < 0.001$ | $P < 0.02$ |

As these data indicate elevated levels of $t^6A$ in urine is a clear marker for all the cancers tested except perhaps Hodgkins disease. The lack of significant variation in the Hodgkins patients may be attributable to the small number of patients involved.

EXAMPLE 2

Monoclonal Antibody Preparation.

A Balb/C mouse was immunized with the $t^6A$-BSA conjugate of Example 1 (100 μg) in complete Freund's adjuvant intraperitoneally at day 0. At day 7 the mouse was boosted with 100 μg of the conjugate in PBS intravenously. The mouse spleen was removed at day 10. Spleen cells were fused with P3/63/Ag 8.653 murine myeloma cells according to Kennet's fusion protocol (Kennet, et al, (1979) *Cell Fusion*. In Methods in Enzymology, Academic Press, New York pp 345-357). The fusogen was polyethylene glycol (1540 mw) at 38% w/v.

Media from wells containing surviving cells were tested for anti-$t^6A$ antibody by radioimmunoassay. Cells from one of the positive wells (#G8) were subcloned by limiting dilution into wells containing normal mouse spleen cells as feeders. Subclones were tested for antibody production by radioimmunoassay and one, identified as G8-3, was chosen as a source of monoclonal anti-$t^6A$ antibody.

Cells from clone G8-3 were then frozen, reestablished in culture, and subcloned a second time in vitro according to the same procedure as the first sub-cloning. Two sub clones from the second subcloning were retained (#9D4 and #5C4). Cells from line #9D4 were selected to be the established cell line.

The screening of the clones was done using a solid phase assay. A conjugate of $t^6A$ to human serum albumin was made and used to coat wells of a microtiter plate. Culture fluid was then added followed by a second antibody which was labeled with $^{125}I$ and which recognizes mouse IgG. A sample of line #9D4 was deposited in the American Type Culture Collection 12301 Parklawn Drive, Rockville, Md. 20852, USA on Aug. 23, 1983. This sample was assigned ATCC number HB 8351.

Protein from the culture fluid of #9D4 was isolated by means of an affinity column chromatography step using Protein A-Sepharose CL-4B. The bound fraction from this column was tested in various quantitative immunoassays for $t^6A$ as described below.

Radioimmunoassay

The SAS-RIA referred to in Example 1 was used. Reaction volume was 300 μl, and the total protein content was normalized using carrier normal rabbit immunoglobulins—typically 300 μg of total protein/assay. Reactions containing 80 μg of the above described fraction, 15 pmol $[^3H]t^6A$ varying concentrations of unlabeled $t^6A$, and carrier protein were incubated for 1 h at 37° C. in borate-saline buffer: 75 mM NaCl, 0.1 M boric acid, 25 mM sodium tetraborate, pH 8.3. After the reactions were cooled on ice, an equal volume of cold SAS was added. The solution was mixed thoroughly, and the incubation was continued for 30 min at 0°C. At the end of the 30-min incubation, the suspensions were centrifuged for 15 min at 4° C. and 9,400×g and the supernatant fluid was removed by aspiration. The pellet was resuspended in 500 μl of ice-cold 50% SAS in borate-saline buffer, mixed, recentrifuged, and drained as before. The washed pellets were then resuspended in 500 μl of borate-saline buffer and transferred to 5 ml of Aquasol scintllation fluid. Radioactivity was measured in a scintillation spectrophotometer. The results are shown in FIG. 1.

ELISAs

Two ELISA techniques were tested: one using alkaline phosphatase, the other horseradish peroxidase (HRP). In each technique, microtiter plates were washed once with tap water and once with distilled water. Then each well was filled with 50 μl of 10 μg/ml $t^6A$ conjugated to human serum albumin (HSA-$t^6A$) in 1 M NaCl and 0.02 M sodium phosphate (pH 7.0), and left overnight at 4° C. Each well was emptied and washed (3×100 μl) with 1% HSA in PBS. Wells were then filled with a solution without antibody or various dilutions of hybridoma culture fluid in PBS. After incubation at room temperature for 2 to 3 h, wells were emptied and washed (3×100 μl) with 1% HSA in PBS. Then each well was incubated with 50 μl of a dilution of enzyme-anti-mouse IgG conjugate. Each type of reaction was then treated differently, as described below.

Alkaline phosphatase

To each well was added 50 μl of a 1/500 dilution of goat anti-mouse IgG conjugated to alkaline phosphatase. After standing at room temperature for 2 to 3 h, the wells were emptied, washed (3×100 μl) with 10% diethanolamine (pH 9.8), and filled with 100 μl of 1 mg/ml p-nitrophenylphosphate in 10% diethanolamine (pH 9.8). The enzyme-substrate reaction was incubated 30 min at room temperature and stopped with 100 μl of 3N NaOH. Absorbance at 405 nm was read in an Automated Microtiter Plate Reader (Micro ELISA Autoreader MR 580, Dynatech).

Horseradish peroxidase

To each well was added 50 μl of a 1/500 dilution of goat anti-mouse IgG conjugated to horseradish peroxidase. After standing at room temperature for 2 to 3 h, the wells were emptied and washed once with water and twice with 0.05% Triton X-100 sufactant in PBS. To each well was added 100 μl of the followng solution: 0.1 ml of 15 mg 2,2'-azino-Dl-(3-ethylbenzthiazoline sulfonic acid) (ABTS) per ml of $H_2O$, 0.33 ml of 0.3% $H_2O_2$, and 10 ml of citrate buffer (0.105 g of citric acid in 10 ml of $H_2O$ adjusted to pH 4.0 using 5 M NaOH). After 30 min, absorbance at 405 nm was read in an Automated Microtiter Plate Reader.

Figure 2:
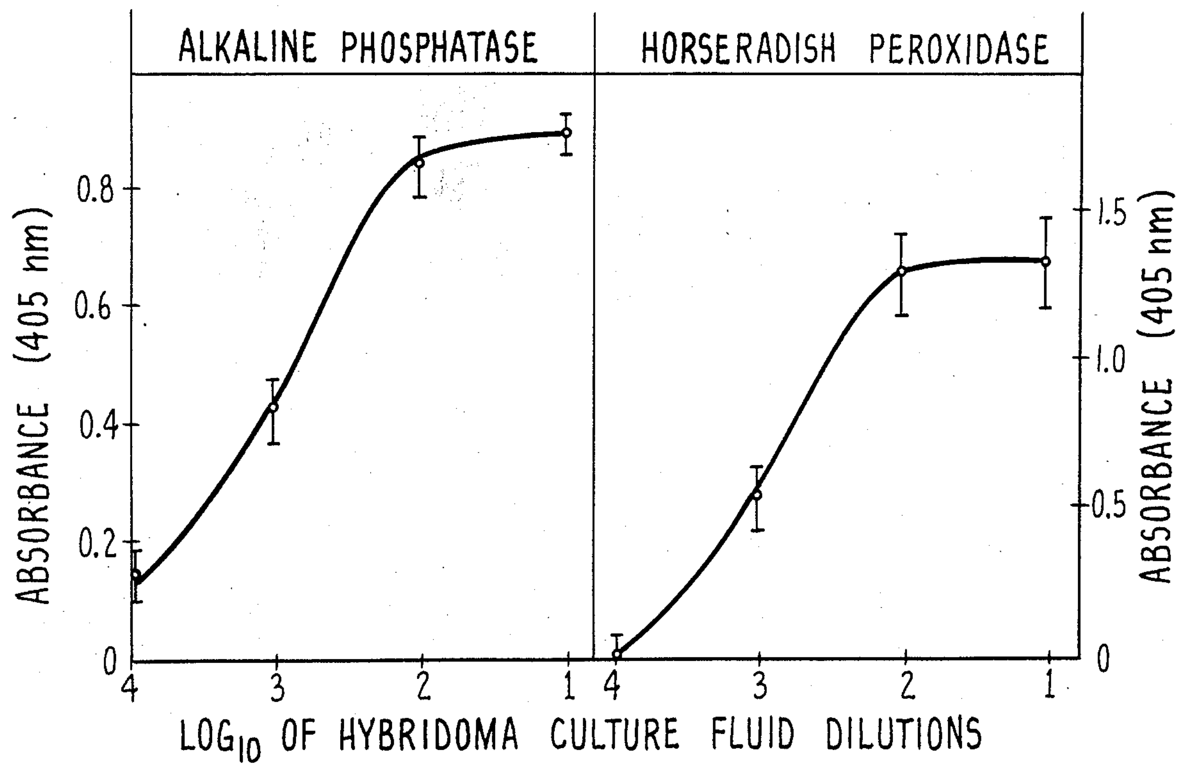
FIG. 2 is a graph showing the results of the two ELISA tests described in Example 2, infra.

FIG. 2 shows the results of these ELISAs.

Figure 3:
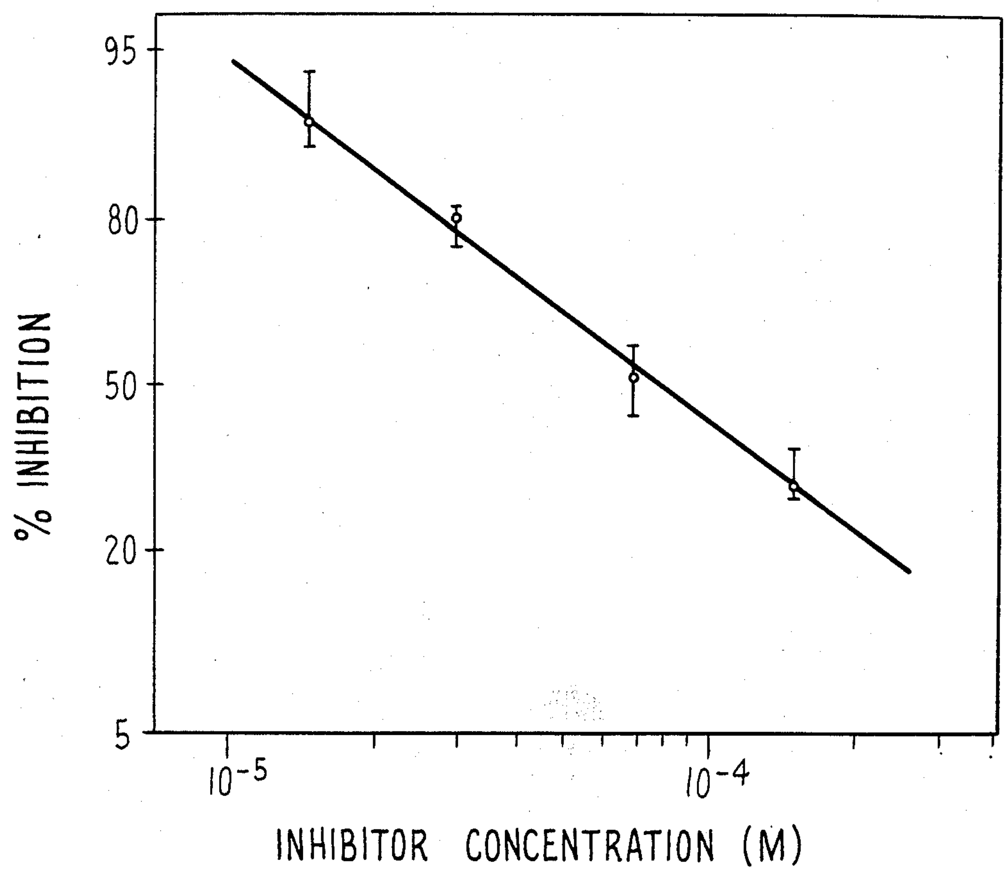
FIG. 3 is a graph showing the results of the competition ELISA test described in Example 2, infra.

A standard curve using a $t^6A$ standard can be prepared for these ELISA techniques using a competitive inhibition procedure in which free $t^6A$ is added to the wells in which the $t^6A$-HSA has been absorbed. A standard curve with the alkaline phosphatase ELISA is shown in FIG. 3. FIG. 3 demonstrates that 50% inhibition of the ELISA was achieved at a concentration of $t^6A$ of $8.4\times10^{-5}$ M. Using the RIA with the monoclonal antibody gave 50% inhibition at $3.2\times10^{-6}$ M. The concentration of $t^6A$ in human urine is approximately $15\times10^{-6}$ M.

Modifications of the above scribed modes for carrying out the invention that are obvious to those of ordinary skill in the immunodiagnostic art and/or related arts are intended to be within the scope of the following claims.

I claim:

1. A method for detecting cancer in a human patient comprising:
   (a) determining the amount of N-[9-(β-D-ribofurano syl)purin-6-ylcarbamoyl]-L-threonin in the urine of said patient; and
   (b) then comparing said amount with the standard amount of N-[9-(β-D-ribofuranosyl)purin-6-ylcarbamoyl]-L-threonine present in the urine of normal human subjects to determine whether said amount is substantially greater than the standard amount, a substantially greater amount being an indication of the presence of cancer.

2. A method for monitoring the status of cancer in a human cancer patient comprising:
   (a) obtaining urine specimens from the patient at predetermined time intervals;
   (b) determining the amounts of N-[9-(β-D-ribofurano syl)purin-6-ylcarbamoyl]-L-threonin ($t^6A$) in the specimens; and
   (c) comparing the amounts, with an increase in amount being an indication of increased tumor burden and a decrease in amount being an indication of decreased tumor burden.

3. The method of claim 2 wherein the cancer is non-Hodgkins lymphoma or a solid tumor.

4. The method of claim 2 wherein the determinations of step (b) are made by a quantitative immunoassay in which the specimen from the patient is incubated with an antibody against $t^6A$ and labeled $t^6A$.

5. The method of claim 2 wherein the determinations of step (b) are made by a competitive inhibition enzyme-linked immunosorbent assay in which a $t^6A$-protein carrier conjugate bound to a solid phase is incubated with the specimen and an antibody against $t^6A$ followed by incubation with an enzyme-labeled antibody against said antibody.

6. The method of claim 4 wherein the antibody against $t^6A$ is a monoclonal antibody produced by hybridoma ATCC HB8351.

7. The method of claim 5 wherein the antibody against $t^6A$ is a monoclonal antibody produced by hybridoma ATCC HB8351.

8. A radioimmunoassay kit for determining the amount of N-[9(β-D-ribofuranosyl)purin-6-ylcarbamoyl]-L-threonin in the urine of a human comprising in packaged combination a multi-container unit having:
   (a) a first container containing radiolabeled N-[9-(β-D-ribofuranosyl)purin-6-ylcarbamoyl]-L-threonin; and
   (b) a second container containing a monoclonal antibody produced by hybridoma ATCC HB8351.

9. An enzyme immunoassay kit for determining the amount of N-[9-(β-D-ribofuranosyl)purin-6-ylcarbamoyl]-L-threonine in the urine of a human comprising in packaged combination a multi-container unit having:
   (a) a first container containing N-[9-(β-D-ribofurano syl)purin-6-ylcarbamoyl]-L-threonine conjugated to a carrier protein;
   (b) a second container containing a monoclonal antibody produced by hybridoma ATCC HB8351; and
   (c) a third container containing an enzyme-labeled antibody against said monoclonal antibody.

* * * * *